US011241543B2

(12) United States Patent
Plumptre

(10) Patent No.: US 11,241,543 B2
(45) Date of Patent: Feb. 8, 2022

(54) BUTTON FOR A DRUG DELIVERY DEVICE AND METHOD FOR ASSEMBLING A BUTTON FOR A DRUG DELIVERY DEVICE

(71) Applicant: Sanofi-Aventis Deutschland GMBH, Frankfurt am Main (DE)

(72) Inventor: David Aubrey Plumptre, Warwick (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 482 days.

(21) Appl. No.: 16/303,462

(22) PCT Filed: May 29, 2017

(86) PCT No.: PCT/EP2017/062872
§ 371 (c)(1),
(2) Date: Nov. 20, 2018

(87) PCT Pub. No.: WO2017/207478
PCT Pub. Date: Dec. 7, 2017

(65) Prior Publication Data
US 2020/0316306 A1  Oct. 8, 2020

(30) Foreign Application Priority Data
May 31, 2016 (EP) .................................. 16172150

(51) Int. Cl.
*A61M 5/315* (2006.01)
*A61M 5/24* (2006.01)
(Continued)

(52) U.S. Cl.
CPC .......... *A61M 5/31581* (2013.01); *A61M 5/24* (2013.01); *A61M 5/3157* (2013.01);
(Continued)

(58) Field of Classification Search
CPC .......... A61M 5/31581; A61M 5/31551; A61M 5/3157; A61M 2005/3126; A61M 5/3158;
(Continued)

(56) References Cited

U.S. PATENT DOCUMENTS 5,735,314 A * 4/1998 Alaze .................... B60T 8/4068
138/31
5,935,691 A 8/1999 Tsai
(Continued)

FOREIGN PATENT DOCUMENTS

CN     102369028     3/2012
CN     102596291     7/2012
(Continued)

OTHER PUBLICATIONS

International Preliminary Report on Patentability in Application No. PCT/EP2017/062872, dated Dec. 4, 2018, 9 pages.
(Continued)

*Primary Examiner* — Theodore J Stigell
(74) *Attorney, Agent, or Firm* — Fish & Richardson P.C.

(57) ABSTRACT

A button for setting and dispensing a dose of a drug from a drug delivery device is described. The button comprises a plastic component and a metal component, wherein the plastic component is at least partly received by the metal component, and wherein the metal component is configured to be manipulated by a user for setting and dispensing the dose. Furthermore, a method for assembling a button for a drug delivery device and a drug delivery device comprising the button are described.

19 Claims, 14 Drawing Sheets

(51) Int. Cl.
*A61M 5/31* (2006.01)
*B23P 19/04* (2006.01)

(52) U.S. Cl.
CPC ....... *A61M 5/3158* (2013.01); *A61M 5/31551* (2013.01); *A61M 2005/3126* (2013.01); *A61M 2205/581* (2013.01); *A61M 2207/00* (2013.01); *B23P 19/04* (2013.01)

(58) Field of Classification Search
CPC .. A61M 5/24; A61M 5/31548; A61M 5/3155; A61M 2205/02
See application file for complete search history.

(56) References Cited

U.S. PATENT DOCUMENTS

| | | | | |
|---|---|---|---|---|
| 2005/0165363 | A1* | 7/2005 | Judson | A61M 5/31551 604/209 |
| 2006/0069355 | A1* | 3/2006 | Judson | A61M 5/31511 604/211 |
| 2011/0092905 | A1 | 4/2011 | Cowe | |
| 2012/0000756 | A1 | 1/2012 | Schnitzler et al. | |
| 2012/0165741 | A1 | 6/2012 | Harms et al. | |
| 2014/0074023 | A1* | 3/2014 | Denning | A61M 5/50 604/110 |
| 2016/0192760 | A1 | 7/2016 | Nishiura et al. | |
| 2016/0206820 | A1* | 7/2016 | Plumptre | A61M 5/31536 |

FOREIGN PATENT DOCUMENTS

| | | |
|---|---|---|
| CN | 105492049 | 4/2016 |
| CN | 105492122 | 4/2016 |
| JP | S54-018651 * | 2/1979 |
| JP | 2012-153444 | 8/2012 |
| JP | 2012-519946 | 8/2012 |
| JP | 2012-521260 | 9/2012 |
| JP | 2012-521836 | 9/2012 |
| JP | 2015-526217 | 9/2015 |
| JP | 2016-506763 | 3/2016 |
| TW | 201529116 | 8/2015 |
| TW | 201603849 | 2/2016 |
| TW | 201603850 | 2/2016 |
| WO | WO 97/13537 | 4/1997 |
| WO | WO 2008/083209 | 7/2008 |
| WO | WO 2010/110712 | 9/2010 |
| WO | WO 2010/112565 | 10/2010 |
| WO | WO-2010112565 * | 10/2010 |
| WO | WO 2014/033195 | 3/2014 |
| WO | WO 2014/111335 | 7/2014 |
| WO | WO 2015/028440 | 3/2015 |
| WO | WO 2015/028441 | 3/2015 |
| WO | WO-2015028441 * | 3/2015 |
| WO | WO 2016/001292 | 1/2016 |
| WO | WO 2016/001304 | 1/2016 |
| WO | WO 2016/006105 | 1/2016 |

OTHER PUBLICATIONS

International Search Report and Written Opinion in Application No. PCT/EP2017/062872, dated Dec. 11, 2017, 14 pages.

* cited by examiner

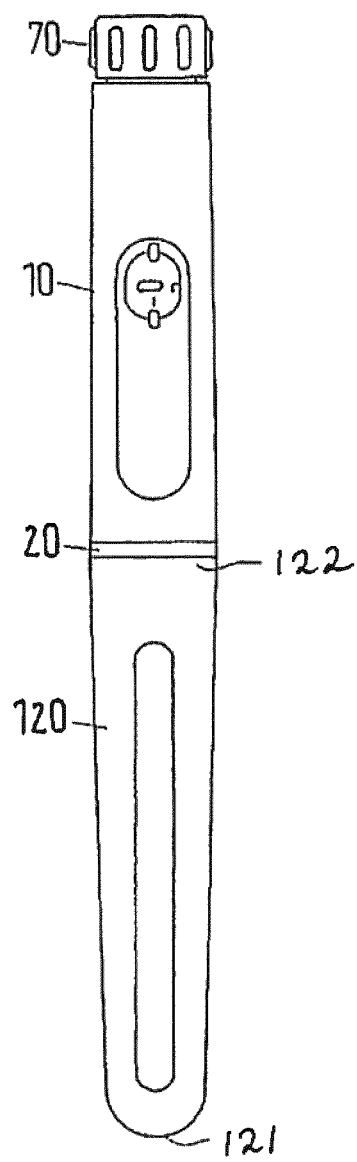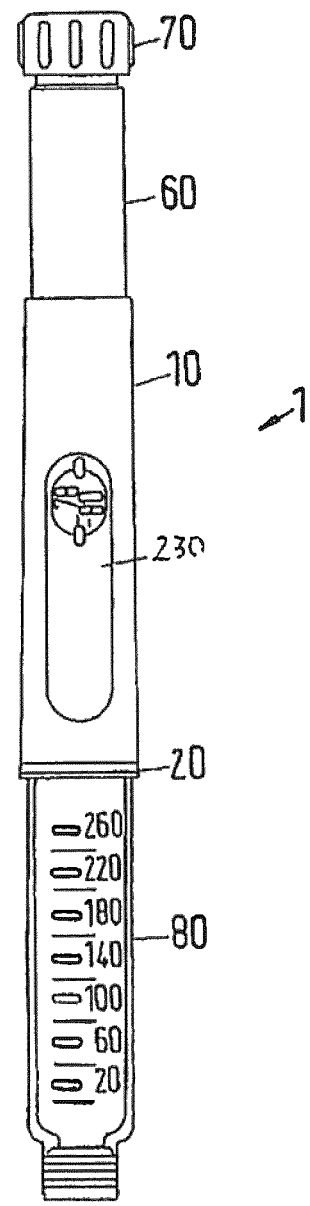

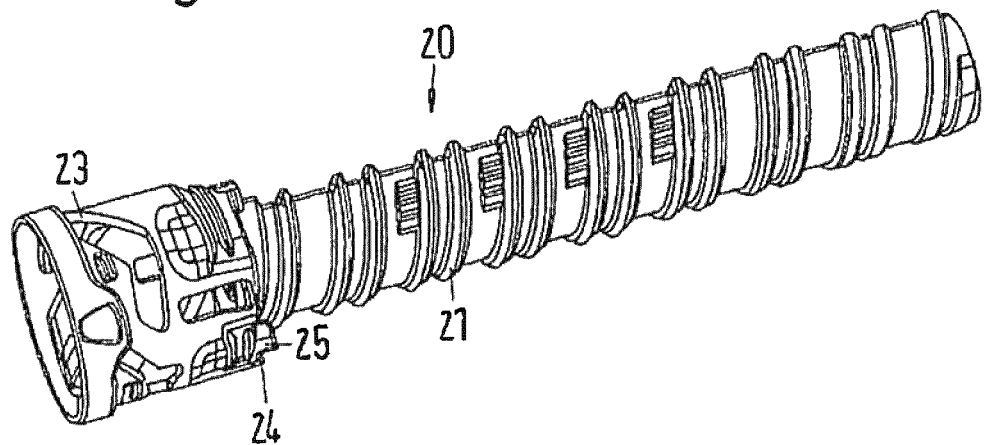
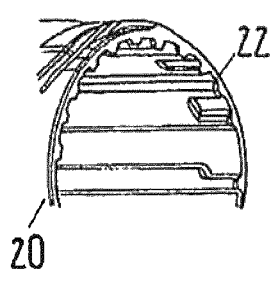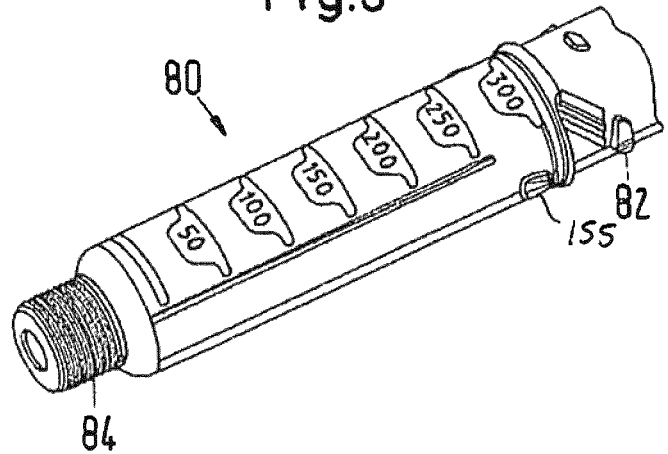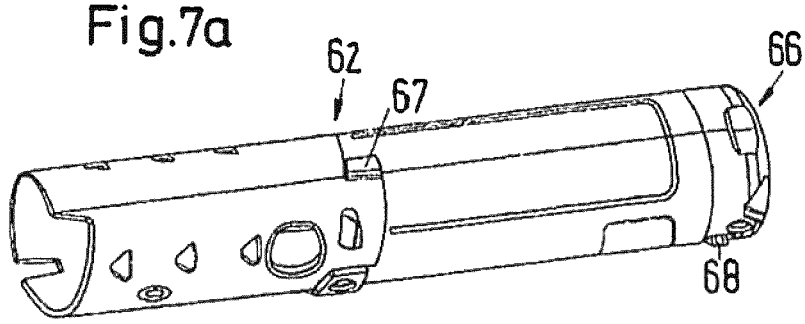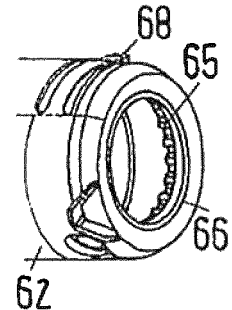

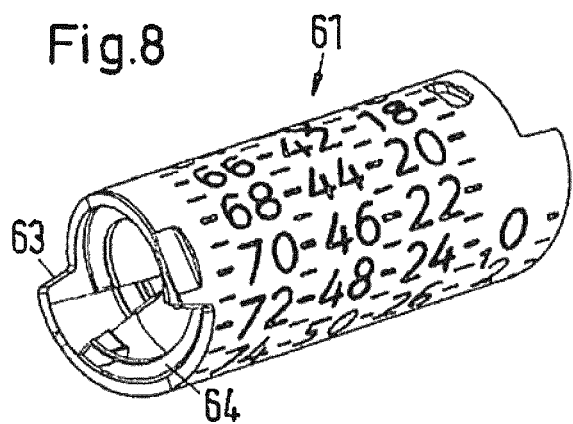
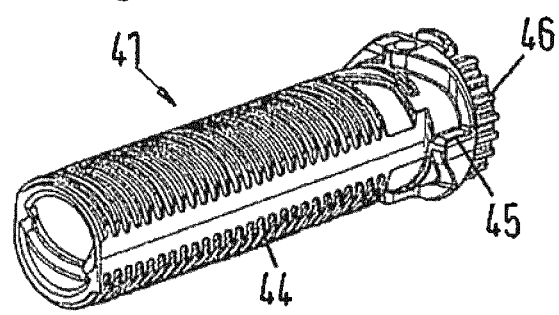
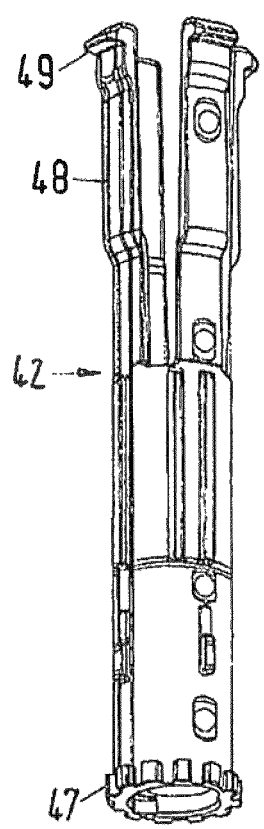
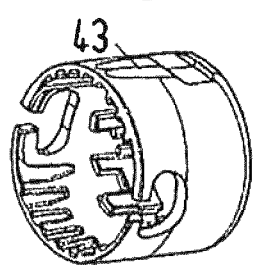
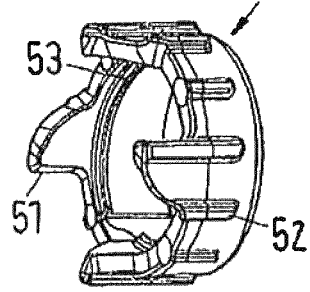

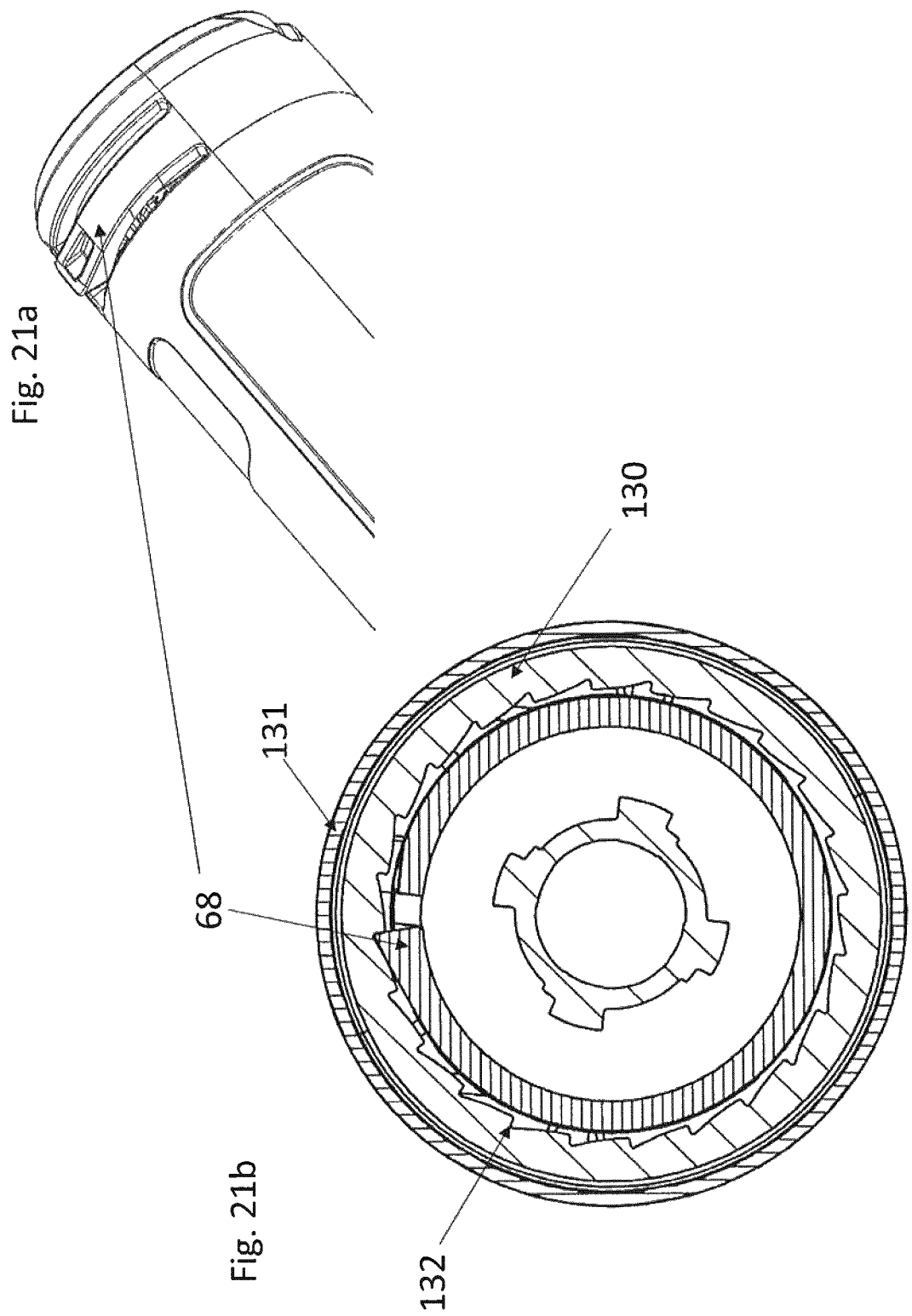

BUTTON FOR A DRUG DELIVERY DEVICE AND METHOD FOR ASSEMBLING A BUTTON FOR A DRUG DELIVERY DEVICE

CROSS REFERENCE TO RELATED APPLICATIONS

The present application is the national stage entry of International Patent Application No. PCT/EP2017/062872, filed on May 29, 2017, and claims priority to Application No. EP 16172150.1, filed on May 31, 2016, the disclosures of which are incorporated herein by reference.

TECHNICAL FIELD

The present disclosure relates to a button for a drug delivery device. Furthermore, the present disclosure relates to a drug delivery device comprising the button and to a method of assembling a button for a drug delivery device.

BACKGROUND

Drug delivery devices, in particular pen-type drug delivery devices, have application where regular injection by persons without formal medical training occurs. This may be increasingly common among patients having diabetes where self-treatment enables such patients to conduct effective management of their disease. In practice, such a drug delivery device allows a user to dispense a number of user-variable doses or fixed doses of a medicament.

There are fundamentally two types of drug delivery devices: resettable (i.e. reusable) devices and non-resettable (i.e. disposable) devices. For example, disposable drug delivery devices do not have removable pre-filled cartridges.

SUMMARY

The present disclosure relates to a button for a drug delivery device. In some cases, the button is especially robust, light-weight and/or cost-effective.

According to one aspect, a button for a drug delivery device is provided. The button is adapted to be used as a button or a dial grip for the device. The button may be adapted for setting and dispensing a dose of a drug from the device once assembled to the device.

The term "drug", as used herein, preferably means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compounds, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivatives.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra-low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two 13 sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are, for example, hydrates.

The button may comprise several components. The button may comprise two components. The button may comprise a plastic component and a metal component. The plastic component may comprise Polyoxymethylene or another plastic material. The plastic component may be produced by injection moulding. The metal component may comprise aluminium, for example. Alternatively, the metal component may comprise another metal material. An outer surface of the metal component may be anodised. The anodising provides a high quality and hard wearing exterior surface to the metal component. Furthermore, the anodising enables the metal component to be given a variety of metallic colours.

The plastic component may be at least partly received by the metal component. Thus, the plastic component may be an inner component of the button. The metal component may be an exterior or outer component of the button. The metal component may be configured to be manipulated by a user for setting and dispensing the dose. In particular, the metal component may be rotated by the user during dose setting. The metal component may comprise an outer surface especially adapted to be gripped by the user. For example, the metal component may comprise at least one grip feature.

Due to the exterior metal component, a high quality and hard wearing exterior surface of the button is provided. Thus, provision of a robust and long-living device is facilitated. Moreover, the surface of the button can be given a variety of metallic colors. In this way, a drug delivery device having a high quality aesthetic is provided. In addition, due to the lightweight inner plastic component, a lightweight and cost-effective device is provided.

According to one embodiment, the metal component comprises an aperture for receiving the plastic component. In other words, the metal component may comprise an open end. A further end of the metal component, which is opposite to the open end, may be at least partly closed. Thus, the metal component may comprise a one-sided open tubular body.

The plastic component may comprise a maximum outer diameter. A diameter of the aperture or open end of the metal component may be smaller than the maximum outer diameter of the plastic component. The plastic component and the metal component may be wedged to one another. In this way, the metal component and the plastic component may be prevented from being separated by the user. Accordingly, a robust and compact button is provided. Hence, provision of a long-living and robust device is facilitated.

According to one embodiment, the plastic component is at least in parts elastically deformable. For example, when compressing the plastic component during assembly of the button, at least parts of the plastic component may elastically flex in a radial inward direction to allow the use of a bump-over design to achieve robust mechanical retention of the metal component. In this way, assembly of the button may be facilitated. Moreover, by means of the plastic component being elastically flexible, a tight interface between the plastic component and the metal component may be ensured when the two components are secured to one another.

According to one embodiment, the metal component is formed over the plastic component. The shape of the plastic component and the metal component may be at least in a portion adapted to each other. In particular, an outer surface of the metal component may be at least in parts adapted to an outer surface of the plastic component.

When assembling the button, compression of the two components may take place. Thereby, the design of the plastic component may allow it to elastically flex inwards so that the metal component can be formed over the plastic component. In this way, a smooth surface of the button may be achieved.

According to one embodiment, the metal component is clamped to the plastic component. In particular, the metal component may be swaged to clamp the plastic component. The metal component may be swaged to the plastic component. Thus, separation of the plastic component and the metal component may be prevented once assembled into the button. In other words, the metal component and the plastic component may be non-releasably connected to one another. Hence, provision of a safe and long-living device is facilitated.

According to one embodiment, the metal component and the plastic component are rotationally coupled to one another. Accordingly, rotation of the metal component during dose setting and/or dose delivery may be transferred into rotation of the plastic component.

For rotationally coupling and/or aligning the metal component and the plastic component, the plastic component may comprise at least one protrusion. The plastic component may comprise a plurality of protrusions, e.g. three protrusions. The protrusions may protrude from an end face of the plastic component. The metal component may comprise at least one cut-out. The metal component may comprise a plurality of cut-outs, e.g. three cut-outs. The cut-outs may be arranged on an end face of the metal component. The cut-outs may be produced by punching.

The protrusion and the cut-out may be adapted and arranged to mechanically cooperate with one another for rotationally coupling and/or aligning the metal component and the plastic component. In particular, the protrusion is received by the cut-out for coupling the plastic component and the metal component. Movement of the metal component and, hence, of the plastic component may be transferred to a drive mechanism of the device. Hence, provision of an effective and reliable device is facilitated.

According to one embodiment, the plastic component comprises at least one grip feature. The grip feature may comprise one, two or more ribs and/or grooves. The grip feature may be arranged on an outer surface of the plastic component. The metal component may comprise at least one mating grip feature. The grip feature may comprise one, two or more ribs and/or grooves. The grip feature may be arranged on an inner surface of the metal component. Preferably, the grip feature of the metal component is arranged on both the outer and the inner surface of the metal component. The grip feature of the metal component may be stamped into the surface of the metal component. However, also other ways of providing the grip feature on the metal component are possible. The grip feature may be part of a deep drawing process of the metal component, for example.

The grip features may be adapted and arranged for aligning the plastic component and the metal component when the plastic component is received by the metal component. Moreover, the grip features may provide torque transmission between the plastic component and the metal component. In other words, the grip features are provided for rotationally coupling the plastic component and the metal component. Torque applied by the user may be transferred through the grip feature of the metal component to the corresponding grip feature on the plastic component and, hence, to the drive mechanism of the device. Moreover, the grip feature of the metal component may enable the user to easily grip the button. Hence, provision of a user-friendly and effective device is facilitated.

According to one embodiment, the metal component is deep drawn. The metal component may be deep drawn from a sheet of metal. After deep drawing, the metal sheet may comprise an end face which is perpendicular with respect to a longitudinal axis of the metal sheet. In this way, the metal component comprising the shape of a tubular body with one side being open is provided.

According to one aspect, a method for assembling a button for a drug delivery device is provided. The button may be the previously described button. The button may comprise a plastic component and a metal component. The plastic component and the metal component may correspond to the components described above. The method may comprise the following steps:

Inserting the plastic component at least partly into the metal component. For this purpose, the metal component may comprise an aperture with a diameter large enough to receive the plastic component at least in parts. The metal component may comprise an open end. The metal component may comprise a tip. The tip may constitute a section of gradually reducing diameter delimiting the open end. A distance between the edges of tip, i.e. the diameter of the aperture, may be large enough to insert the plastic component at least partly. The plastic component may comprise a maximum outer diameter. Before the button is finally assembled, the maximum outer diameter may be less than the diameter of the aperture.

In a next step, the metal component may be swaged to clamp the plastic component for fixedly coupling the metal component and the plastic component. For this purpose, a tool may be provided. The tool may comprise a conical shape. However, also other shapes for the tool are possible. By means of the tool, the open end of the metal component may be swaged to the plastic component. By means of the tool, the open end of the metal component may be compressed and plastically deformed.

The plastic component may comprise a bump feature. The bump feature may be arranged on an outer surface of the plastic component. The bump feature may extend circumferentially around the outer surface of the plastic component. The bump feature may extend as a continuous feature, or may be separated into discrete regions. The metal component, in particular its open end, may be swaged over the bump feature. The metal component may be swaged over the bump feature around the full circumference of the plastic component. Thereby, the metal component, in particular its open end, may be plastically deformed. Thus, the metal component, in particular its open end, may be formed over the plastic component.

When swaging the metal component to the plastic component, the plastic component or at least parts thereof may be elastically deformed in a radial inward direction so that the metal component can be over-formed. Once released, the plastic component may at least partly spring back, hence creating radial pre-load between the components and ensuring a tight interface between the plastic component and the metal component. In this way, a robust button comprising a smooth surface is provided. Thus, provision of a reliable and robust device is facilitated.

According to one aspect, a drug delivery device is provided. The device may comprise a button. The button may comprise the previously described button. The button may be assembled as described above. The device may be a reusable drug delivery device. In other words, the device may comprise an exchangeable cartridge. However, in alternative embodiments, the device may be a disposable device.

The device may comprise a rotatable sleeve. The sleeve may be rotatable during dose setting and during dose delivery. The plastic component may comprise at least one ratchet feature. The plastic component may comprise a plurality of ratchet features, e.g. two, three or more ratchet features. The ratchet feature may be arranged on an inner surface of the plastic component. The ratchet feature may be adapted and arranged to mechanically cooperate with the sleeve, e.g. with a corresponding ratchet feature of the sleeve, during dose delivery to provide an audible feedback. The audible feedback may indicate to the user that the device is dispensing the drug when the button is depressed after having been dialed up. In this way, a user-friendly device is provided.

According to an embodiment, the device comprises a drive mechanism. The drive mechanism may be an inner part of the device adapted and arranged to transfer movement of the button through the device for expelling the drug. The drive mechanism may comprise the previously mentioned sleeve, for example. The plastic component may comprise at least one snap feature. The plastic component may comprise a plurality of snap features, e.g. two, three, four or more snap features. The snap feature may protrude from the plastic component in a longitudinal direction. The snap feature may be adapted and arranged to mechanically cooperate with the drive mechanism of the device or with components of the drive mechanism for rotationally coupling the button and the drive mechanism. In this way, a reliable and effective device is provided.

Of course, features relating to different aspects or embodiments described above and below may be combined with each other.

BRIEF DESCRIPTION OF THE FIGURES

Further features and refinements become apparent from the following description of exemplary embodiments in connection with the accompanying figures.

FIG. 1 schematically shows a drug delivery device with a cap attached in accordance with the present disclosure;

FIG. 2 schematically shows the drug delivery device of FIG. 1 with the cap removed and a dose of 79 units dialed;

FIG. 5a schematically shows the inner body of the drug delivery device of FIG. 1;

FIG. 5b schematically shows a detail of the inner body of FIG. 5a;

FIG. 6 schematically shows the cartridge holder of the drug delivery device of FIG. 1;

FIG. 7a schematically shows a first display member component of the drug delivery device of FIG. 1;

FIG. 7b schematically shows a detail of the first display member of FIG. 7a;

FIG. 8 schematically shows a second display member component of the drug delivery device of FIG. 1;

FIG. 9 schematically shows a first driver component of the drug delivery device of FIG. 1;

FIG. 10 schematically shows a second driver component of the drug delivery device of FIG. 1;

FIG. 11 schematically shows a third driver component of the drug delivery device of FIG. 1;

FIG. 12 schematically shows the last dose nut of the drug delivery device of FIG. 1;

FIG. 21a schematically shows an inner perspective view of the proximal part of the drug delivery device of FIG. 1;

FIG. 21b schematically shows a cut-away view of the proximal part of the drug delivery device of FIG. 21a;

FIG. 23 schematically shows a method step of assembling the button of FIG. 22a;

DETAILED DESCRIPTION

FIGS. 1 and 2 show a drug delivery device 1 in the form of an injection pen. The device 1 has a distal end (lower end in FIG. 1) and a proximal end (upper end in FIG. 1). The term "distal end" may refer to that end of the device or a component thereof which is or is to be arranged closest to a dispensing end of the device. The term "proximal end" may refer to that end of the device or the component which is or is to be arranged furthest away from the dispensing end of the device 1.

Figure 3:
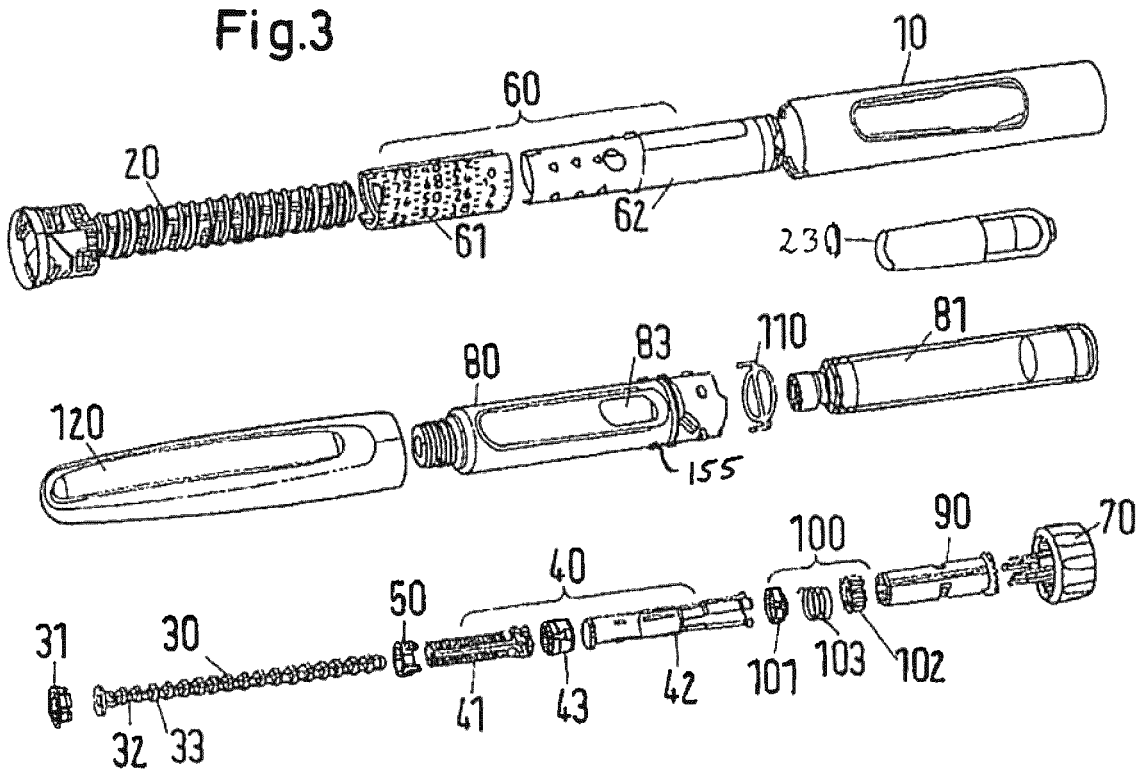
FIG. 3 schematically shows an exploded view of the components of the drug delivery device of FIG. 1.

The components of the drug delivery device 1 are shown in FIG. 3 in more detail. The drug delivery device 1 comprises an outer housing part 10, an inner body 20, a piston rod 30, a driver 40, a nut 50, a display member 60, a button 70, a cartridge holder 80 for receiving a cartridge 81, a clutch 90, a clicker 100, a spring 110, a cap 120 and a window insert 230. A needle arrangement (not shown) comprising a needle hub and a needle cover may be provided as additional components, which can be exchanged. The piston rod 30 comprises a bearing 31. The driver 40 comprises a distal driver part 41, a proximal driver part 42 and a coupler 43. The display member 60 comprises a number sleeve 61 and a dial sleeve 62. The clicker 100 comprises a distal clicker part 101, a proximal clicker part 102 and a spring 103.

Figure 4:
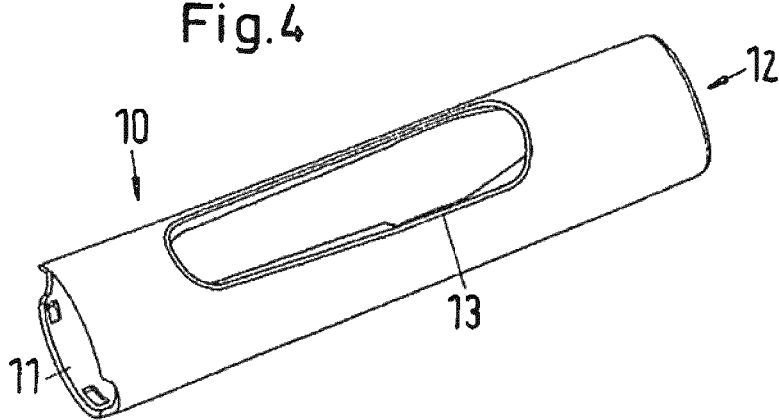
FIG. 4 schematically shows the outer housing of the drug delivery device of FIG. 1.
Figure 13:
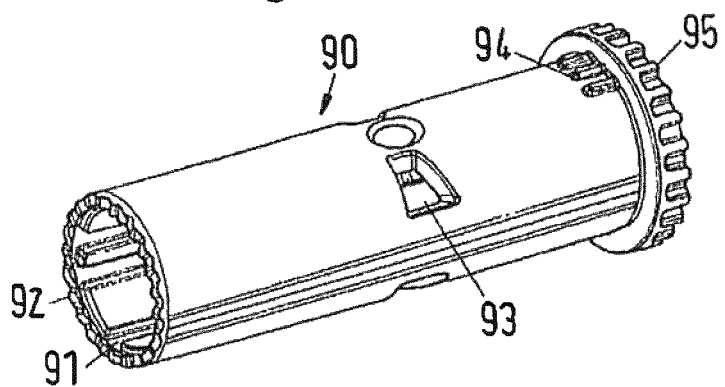
FIG. 13 schematically shows a clutch component of the drug delivery device of FIG. 1.
Figure 14:
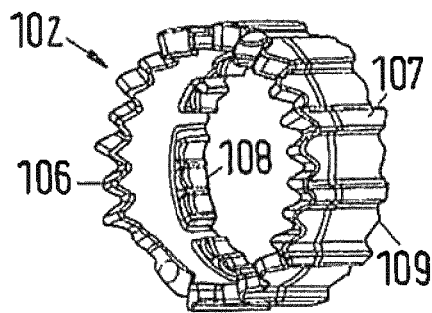
FIG. 14 schematically shows a first clicker component of the drug delivery device of FIG. 1.
Figure 15:
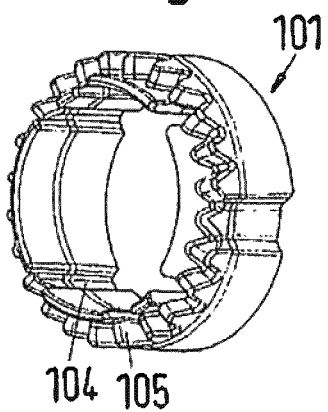
FIG. 15 schematically shows a second clicker component of the drug delivery device of FIG. 1.
Figure 16:
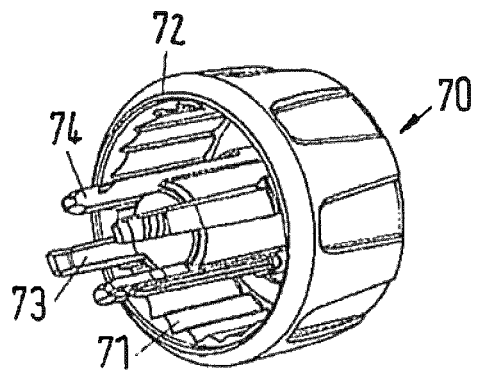
FIG. 16 schematically shows the button of the drug delivery device of FIG. 1.

The outer housing part 10, which is also shown in FIG. 4, is a generally tubular element having a distal part 11 for attaching the inner body 20 and a proximal part, which is provided with a rotational hard stop 12 on its inner surface (not shown) which contact mating faces of the display member 60 when the maximum units (e.g. 80 U) stop is engaged. The end face also serves as the end-of-dose dispense stop for the button 70, and the bore in the end face centers the display member 60 during both dialing and dispense. An aperture 13 is provided for receiving the window insert 230. The outer body 10 provides the user with a surface to grip and react against during dispense.

Figure 17:
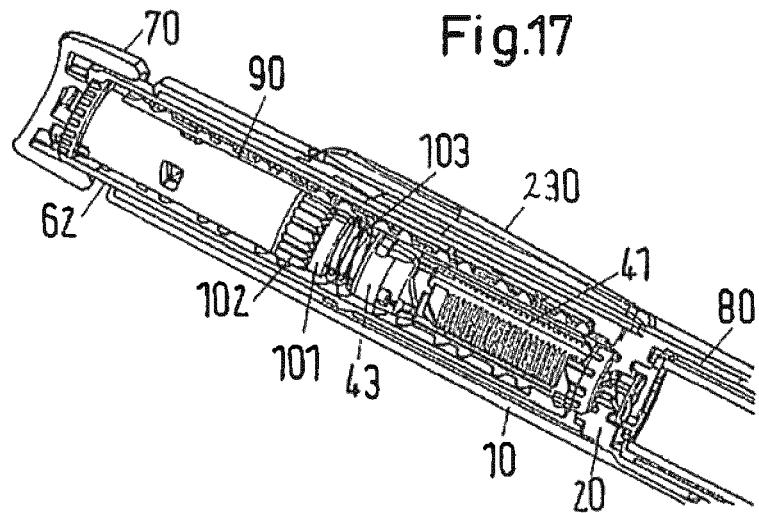
FIG. 17 schematically shows a cut-away view of the proximal part of the drug delivery device of FIG. 1 in a zero unit position with the button released.
Figure 18:
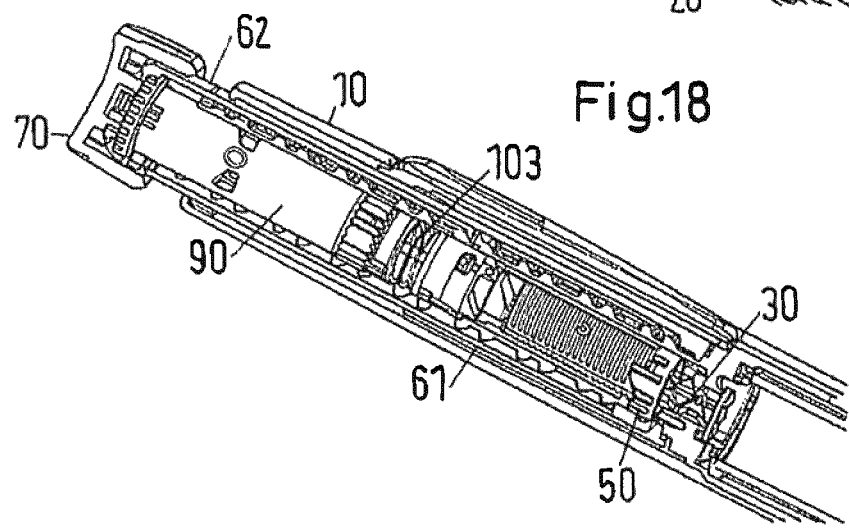
FIG. 18 schematically shows a cut-away view of the proximal part of the drug delivery device of FIG. 1 in a position with some units dialed.
Figure 19:
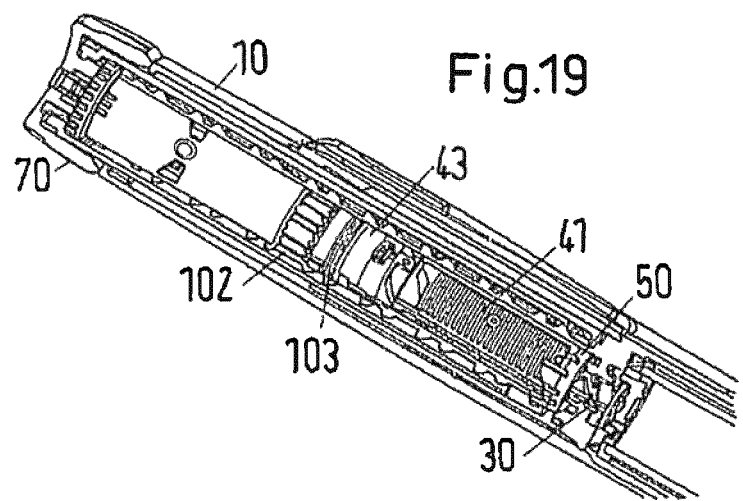
FIG. 19 schematically shows a cut-away view of the proximal part of the drug delivery device of FIG. 1 in a zero unit position with the button pressed.
Figure 20:
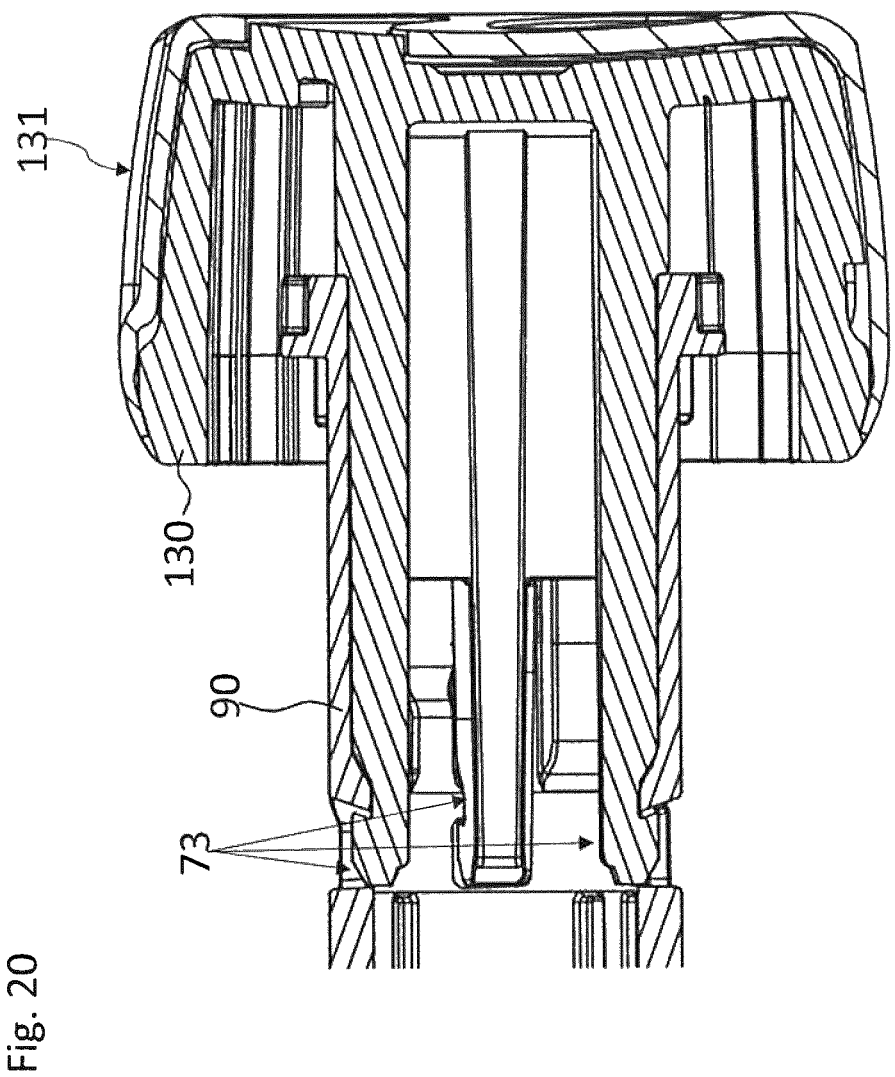
FIG. 20 schematically shows a cut-away view of the proximal part of the drug delivery device of FIG. 1.

The inner body 20 is a generally tubular element having different diameter regions. As can be seen in FIGS. 17 to 19, the inner body 20 is received in the outer body 10 and permanently fixed therein to prevent any relative movement of the inner body 20 with respect to the outer body 10. The inner body has the functions to house the drive mechanism within, guiding the clickers and the last dose nut 50 via internal splines, to provide an internal thread through which the piston rod 30 (lead screw) is driven, to support and guide the number sleeve 61 and the dial sleeve 62 on an external thread form, to secure the cartridge holder 80 and to secure the outer body 10 and the window insert 230.

The outermost diameter of the inner body 20 also forms part of the visual design and remains visible when the cap 120 is secured to the cartridge holder 80 as a ring separating the cap 120 from the outer body 10. This visible ring also has depressions which align with the cap snap features on the cartridge holder 80 to indicate that the cartridge holder has been correctly fitted.

An external thread 21 is provided on the outer surface of the inner body 20. Further, splines 22 (FIG. 5b) are provided on the inner surface of the inner body 20. These internal splines 22 guide the clicker 100 axially during both dialing and dispense and also prevent the last dose nut 50 from rotating. Some of the splines 22 may be wider to ensure correct rotational assembly of the internal components, and these wider splines may have a stepped entry and angled surface to encourage the last dose nut 50 to rotate up against the stop face on the distal drive sleeve 41 during assembly. At the open end shown in FIG. 5b there are an additional short splines which together with the alternating long splines 22 are used to rotationally lock the button 70 (dose dial grip) at the end of dispense and serve to increase the strength of the 0 U dial stop when the button 70 is depressed. This is achieved by engagement with male spline features on the clutch component 90.

Bayonet features 23 guide the cartridge holder 80 into the mechanism during cartridge replacement, compressing the cartridge bias spring 110, and then back off the cartridge holder 80 a small distance in order to reduce axial play in the mechanism. Snap features inside the inner body 20 lock the cartridge holder 80 rotationally when it has been correctly fitted. The profile of these snaps aims to prevent the user from partially fitting the cartridge holder 80, the cartridge bias spring 110 ejecting the cartridge holder 80 if the snaps have not at least started to engage. A window retention nose 24 retains the window insert 230 when the outer body 10 and window insert 230 assembly is axially inserted onto the inner body 20. Two diametrically opposite stop faces 25 define the rotational end position for the number sleeve 61. This end position is the end of dose detent position for the minimum dose (0 U).

The piston rod 30 is an elongate element having two external threads 32, 33 with opposite hand which overlap each other. One of these threads 32 engages the inner thread of the inner body 20. A disk-like bearing 31 is provided at the distal end of the piston rod 30. The bearing 31 may be a separate component as shown in FIG. 3 or may be attached to the piston rod 30 as a one-piece component via a predetermined breaking point.

The piston rod 30 transfers the dispense load from the driver 40 to the bearing 31, creating a mechanical advantage greater than 1:1 by converting the torque generated on the piston rod 30 by the driver 40 thread interface into additional axial load as the piston rod passes through the thread in the inner body 20. The piston rod 30 is reset by pressing on the bearing 31 and this in turn rotates the piston rod back into the inner body 20. This disengages and then rotates the distal drive sleeve 41, resetting the last dose nut 50 back to its starting position on the distal drive sleeve 41.

The driver 40 is a generally tubular element having in the embodiment shown in the Figures three components which are depicted in FIGS. 9 to 11 in more detail.

The distal drive sleeve 41 engages with the piston rod thread 33 to drive the piston rod 30 through the inner body 20 during dose delivery. The distal drive sleeve 41 is also permanently connected to the coupler 43 which in turn is releasably engaged through reset clutch features to the proximal drive sleeve 42. The two halves of the drive sleeve 41 are rotationally and axially connected during dialing and dispense, but are de-coupled rotationally during device reset so that they can rotate relative to each other.

The external thread 44 engages with the last dose nut 50. The thread form has three stages, a shallow first stage (left hand side in FIG. 9) over which the nut 50 travels to count the majority of the units dialed, a fast stage over which the last dose nut moves rapidly axially prior to engaging the stop faces, and a final shallow section which ensures that when the stop faces have engaged, the axial restraint on the nut 50 extends over a reasonable length of thread form. Four equi-spaced stop faces 45 engage with mating stop faces 51 on the last dose nut 50 to limit the number of units that can be dialed. Splines 46 are provided at the proximal end of distal drive sleeve 41 to transfer torque from or to the coupler 43, which may be snapped on the distal drive sleeve 41.

The proximal drive sleeve 42 shown in FIG. 10 supports the clicker components 100 and the clutch 90 and transfers rotational movement from the dose button 90 to the coupler 42 and distal drive sleeve 41.

Teeth features 47 located at the distal end of proximal drive sleeve 42 engage with the reset clutch features on the coupler 43 to connect both halves of the drive sleeve during dialing and dispense. During reset these teeth 47 disengage.

Several splines are provided on the outer surface of proximal drive sleeve 42 engaging with distal proximal clicker part 102, preventing relative rotation during dialing and dispense. Further splines, which are located in the middle region of proximal drive sleeve 42, engage with the clutch 90 component. They may be arranged to be non-rotationally symmetric so that the various clicker components cannot be assembled accidentally upside down.

The proximal portion of proximal drive sleeve 42 has four arms or fingers 48, as can be seen in FIG. 10. A hook-like bearing surface 49 exists on the underside (as seen in FIG. 10) of flange segments on the end of the flexible fingers 48. The flexible fingers 48 are separated with gaps or slots that make space for the button 70 to snap to the clutch 90 and also enable these fingers to flex inwards during assembly of the proximal drive sleeve 42 to the dial sleeve 62. After assembly the hooks 49 retain the proximal drive sleeve 42 relative to the dial sleeve 62 under the reaction force from the spring 103. During dispense the button 70 depresses the spring 103 via the clutch 90 and the clicker components and this spring 103 is reacted through the coupler 43 to the proximal drive sleeve 42 which then through these bearing surfaces applies axial load to the dial sleeve 62. This axial load drives the dial sleeve 62 and hence number sleeve 61 along the helical thread of the inner body 20, back into the body of the device 1, until the 0 U stop faces on the number sleeve 61 contact the inner body 20.

The coupler 43 shown in FIG. 11 rotationally couples the two halves of the drive sleeve 42 together during dialing and dispense, whilst allowing them to de-couple during reset. The coupler 43 has to also transfer the last dose protection stop load from the proximal drive sleeve 42 to the distal drive sleeve 41. Two sets of teeth are provided in the coupler 43 for engaging teeth 46 and teeth 47, respectively. The coupler 43 is snapped onto distal drive sleeve 41 allowing limited relative axial movement with respect to the proximal drive sleeve 42.

The nut 50 is provided between the inner body 20 and the distal drive sleeve 41 of driver 40. Stop faces 51 are located on the proximal face of last dose nut 50 to limit the number of units that can be dialed if the stop faces 51 contact stops 45 of distal drive sleeve 41. The function of the last dose nut 50 is to prevent the user from dialing beyond a finite amount. This limit is based on the dispensable volume of the cartridge 81 and when reached, the user must replace the cartridge 81 and reset the device.

External ribs 52 of the nut 50 engage splines 22 of inner body 20. An internal thread 53 of the nut engages the external thread 44 of distal drive sleeve 41. As an alternative, splines and ribs could be provided on the interface between the nut 50 and the driver 40 and threads could be provided on the interface between the nut 50 and the inner body 20. As a further alternative, the nut 50 may be designed as e.g. a half nut.

The display member 60 is a generally tubular element which is composed of number sleeve 61 and dial sleeve 62 which are snapped together during assembly to axially and rotationally constrain these two components, which thus act as a single part.

The main functions of the number sleeve 61 depicted in FIG. 8 are to provide a surface onto which dose numbers can be printed to display the dialed dose, to guide the helical path of the internal mechanism during dialing to follow the helical thread form on the piston rod 30 when threaded to the inner body 20 and to attach to the dial sleeve 62.

The number sleeve 61 is designed to be fully enclosed in the outer body 10 during dialing and dispense and therefore only the dialed dose is visible to the user through the window aperture. The number sleeve has a 0 U (minimum dose) stop face 63 to limit its travel when dialed in but the 80 U (maximum dose) stop faces that limit the dialed out condition are located on the dial sleeve 62. At the end of each dispense stroke, this stop face 63 engages with mating surface 25 on the inner body 20 to limit the rotational position of the number sleeve 61.

A helical drive face 64 forms a thread that guides the number sleeve 61 during dialing and dispense to follow the helical path 21 on the inner body.

The dial sleeve 62 is assembled to the number sleeve 61 such that once assembled, no relative movement is allowed. The parts are made as separate components to enable both molding and assembly. Also, whereas the number sleeve 61 is preferably white to give contrast for the e.g. black dose numbers, the dial sleeve 62 color can be chosen to suit the aesthetics or perhaps to distinguish the drug type.

At the dose proximal end, the dial sleeve 62 has internal clutch features 65 that engage with the clutch 90 during dialing and disengage from the clutch 90 during dispense. These clutch features 65 rotationally lock the dial sleeve 62 to the clutch 90 during dialing and when the 0 U and 80 U stops are engaged. When the button 70 is depressed, these clutch features disengage to allow the clutch 90 and drive mechanism to move axially whilst the dial sleeve 62 and number sleeve 61 spin back to the 0 U start position.

The dial sleeve 62 rotates out during dialing through its engagement with the clutch 90 and number sleeve 61, and rotates back in during dispense under the axial force applied by the proximal drive sleeve 42 to a flange-like bearing face 66 on the end of the dial sleeve. This bearing face 66 engages with the flexible arms 48 of the proximal drive sleeve 42 during dispense. Two diametrically opposite faces 67 engage with the outer body 10 when the maximum dose (e.g. 80 U) has been dialed, forming the maximum dose stop faces.

The dial sleeve 62 comprises a clicker or ratchet arm 68 (FIGS. 7a, 7b, 21a and 21b). The ratchet arm 68 protrudes from the dial sleeve 62 in a radial outward direction. The ratchet arm 68 engages with a ratchet feature 132 on the button 70 (dose dial grip) to provide audible feedback during dispense, giving one click per unit delivered. Further, this prevents the user from gripping and rotating the number sleeve 61 outwards from a partially dialed out position whilst holding the button 70 pressed in. This would back wind the piston rod 30 which would result in an under dose on the subsequent dialed dose. It may further strengthen the 0 U stop.

The button 70, which is shown in FIGS. 16 and 20 to 26 in more detail, serves as a dose dial grip. The button 70 comprises two components. The two components are coupled to one another such that relative rotational and axial movement between the two components is prevented. In this embodiment, the two components are non-releasably connected to one another. In other words, the two components cannot be separated without destroying the button 70. In an alternative embodiment, the two components may be releasably connected to one another.

Figure 22A:
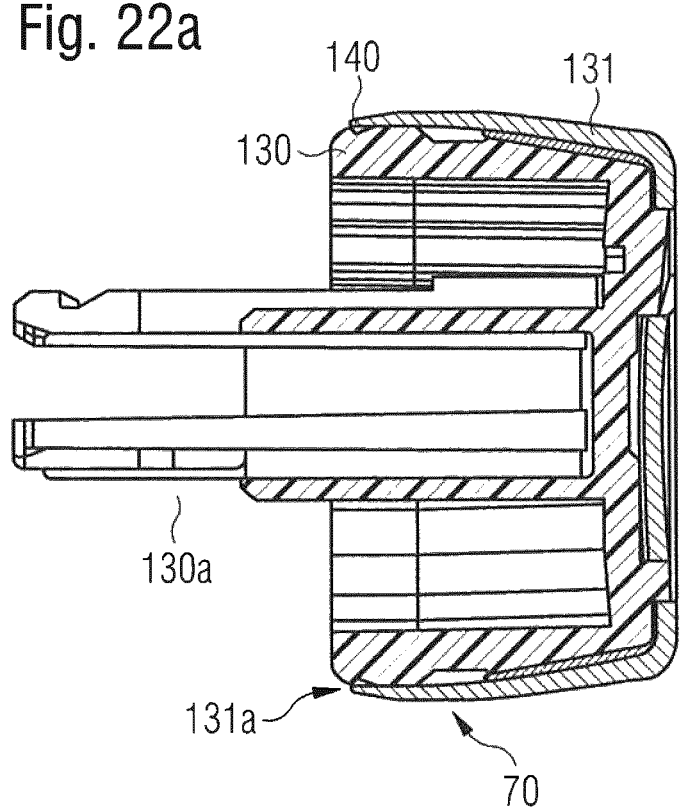
FIG. 22a schematically shows a cut-away view of a dose button of the device of FIG. 1 before final assembly.
Figure 22B:
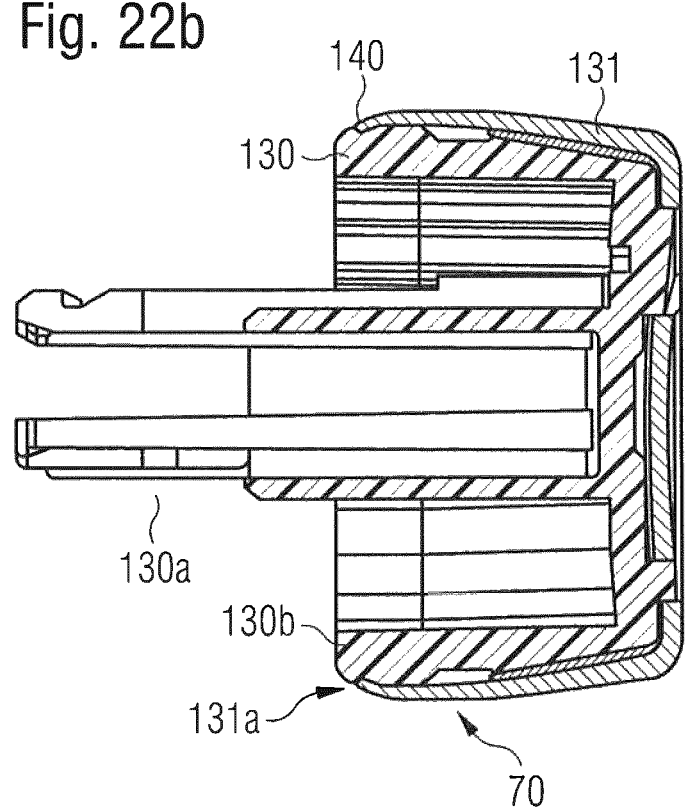
FIG. 22b schematically shows a cut-away view of a dose button of the device of FIG. 1 after final assembly.

The button 70 comprises an inner component or plastic component 130 as can be seen in FIGS. 20, 21b, 22a and 22b, for example. The plastic component 130 comprises a plastic liner. The plastic component 130 is injection moulded, for example. The plastic component 130 comprises a central portion 130a (FIGS. 22a and 22b). The central portion 130a protrudes from the plastic component 130 in a distal direction when the button 70 is assembled to the device 1. The plastic component 130 comprises a proximal portion 130b. The proximal portion 130b is similar to a button in shape. The proximal portion 130b has a greater outer diameter than the central portion 130a. The central portion 130a and the proximal portion 130b are integrally formed.

The button 70 further comprises an outer component or metal component 131 (FIGS. 20, 21b and 22a, 22b). The metal component 131 comprises a metal shell. The metal component 131 comprises aluminum, for example. Alternatively, the metal component 131 may comprise another metal material. The metal component 131 may be deep drawn.

The metal component 131 is of tubular shape. The metal component 131 comprises a hollow body. The metal component 131 is open on one side. In particular, the metal component 131 comprises an aperture 131a or open end. The aperture 131a is located in a distal portion of the metal component 131. The proximal portion of the metal component 131 is at least partly closed. The metal component 131 is arranged around the plastic component 130 as described later on in detail. The metal component 131 is arranged on an outer surface of the button 70 to be manipulated by the user during operation of the device 1.

The metal component 131 and the plastic component 130 are rotationally and axially coupled to one another. For this purpose, the plastic component 130 comprises at least one protrusion 139 (FIG. 25b). In this embodiment, the plastic component 130 comprises three protrusions 139. The protrusions 139 may comprise a logo feature designed for identifying the device 1 and/or the manufacturer of the device 1, for example. The protrusions 139 may be shaped equally, for example. Alternatively, the protrusions 139 may comprise different shapes. For example, one protrusion 139 may be longer than the other protrusions 139. The protrusions 139 may comprise the shape of circular segments. The protrusions 139 may be arranged like segments of a circle. The protrusions 139 protrude from the plastic component 130 in the proximal direction. The protrusions 139 are arranged on a proximal end face of the plastic component 130. The protrusions 139 are arranged on the proximal end face of the proximal portion 130b.

Figure 25A:
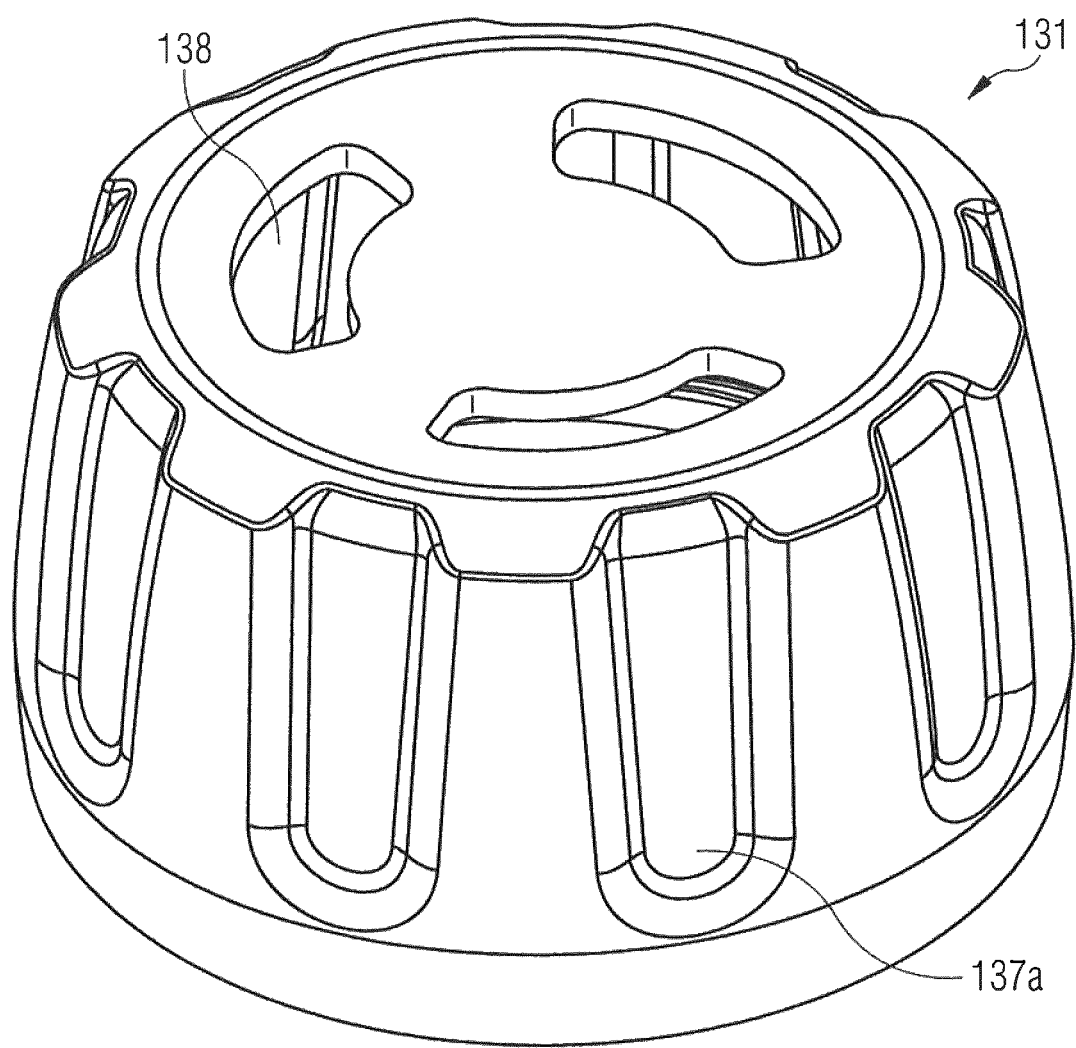
FIGS. 25a & 25b schematically show the components of the dose button of FIG. 22a before assembly.
Figure 25B:
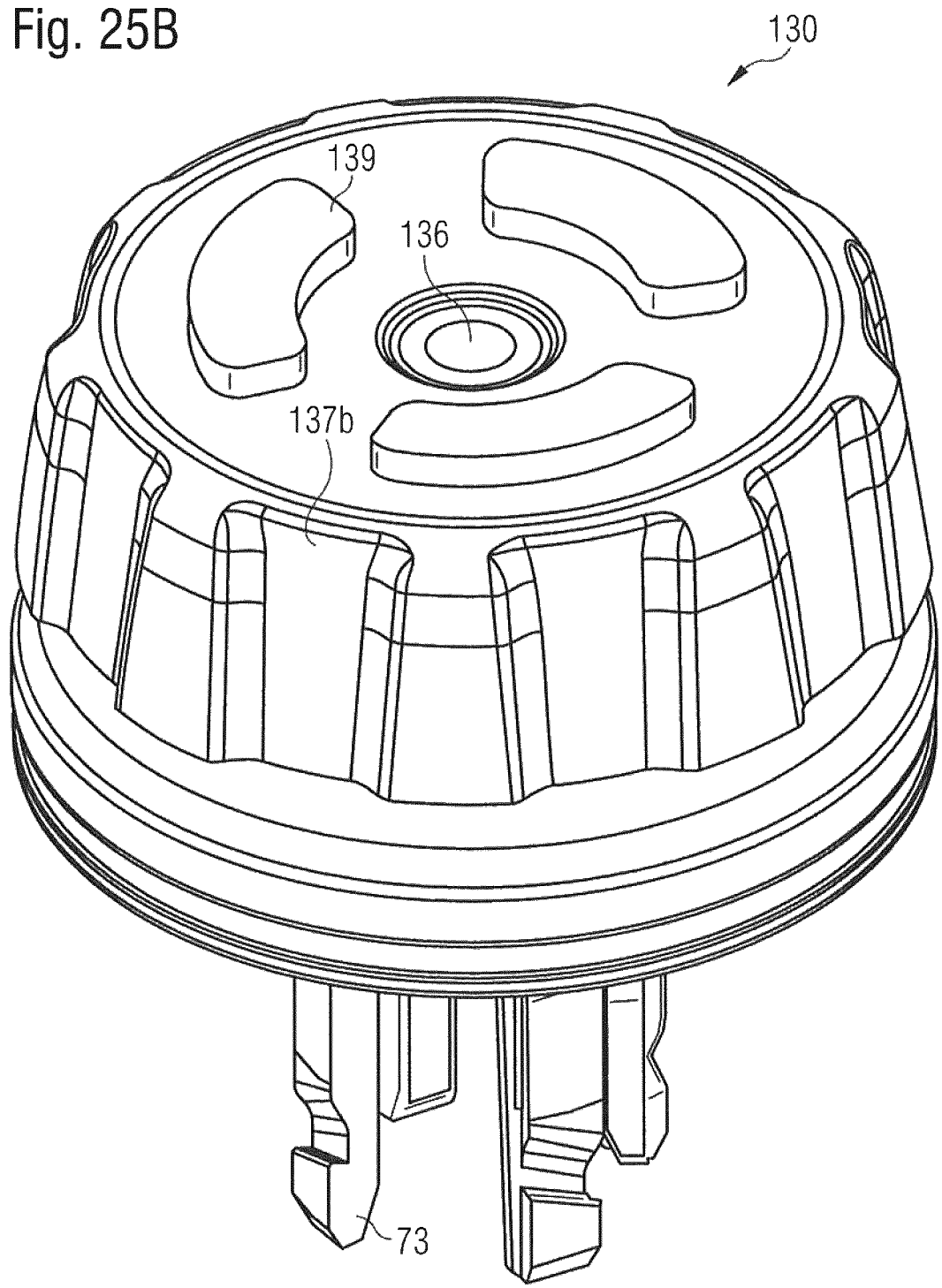

The metal component 131 comprises at least one cut-out 138 (FIG. 25a). In this embodiment, the metal component 131 comprises three cut-outs 138. The cut-outs 138 are arranged on the proximal portion of the metal component 131. The cut-outs 138 are arranged on a proximal end face or top face of the metal component 131. The cut-outs 138 may be punched into the metal component 131. The cut-outs 138 are adapted and arranged to mechanically cooperate with the protrusions 139 of the plastic component 130. When the button 70 is assembled, the protrusions 139 are received by the cut-outs 138 to rotationally align the plastic component 130 and the metal component 131 (FIG. 22b).

Figure 26:
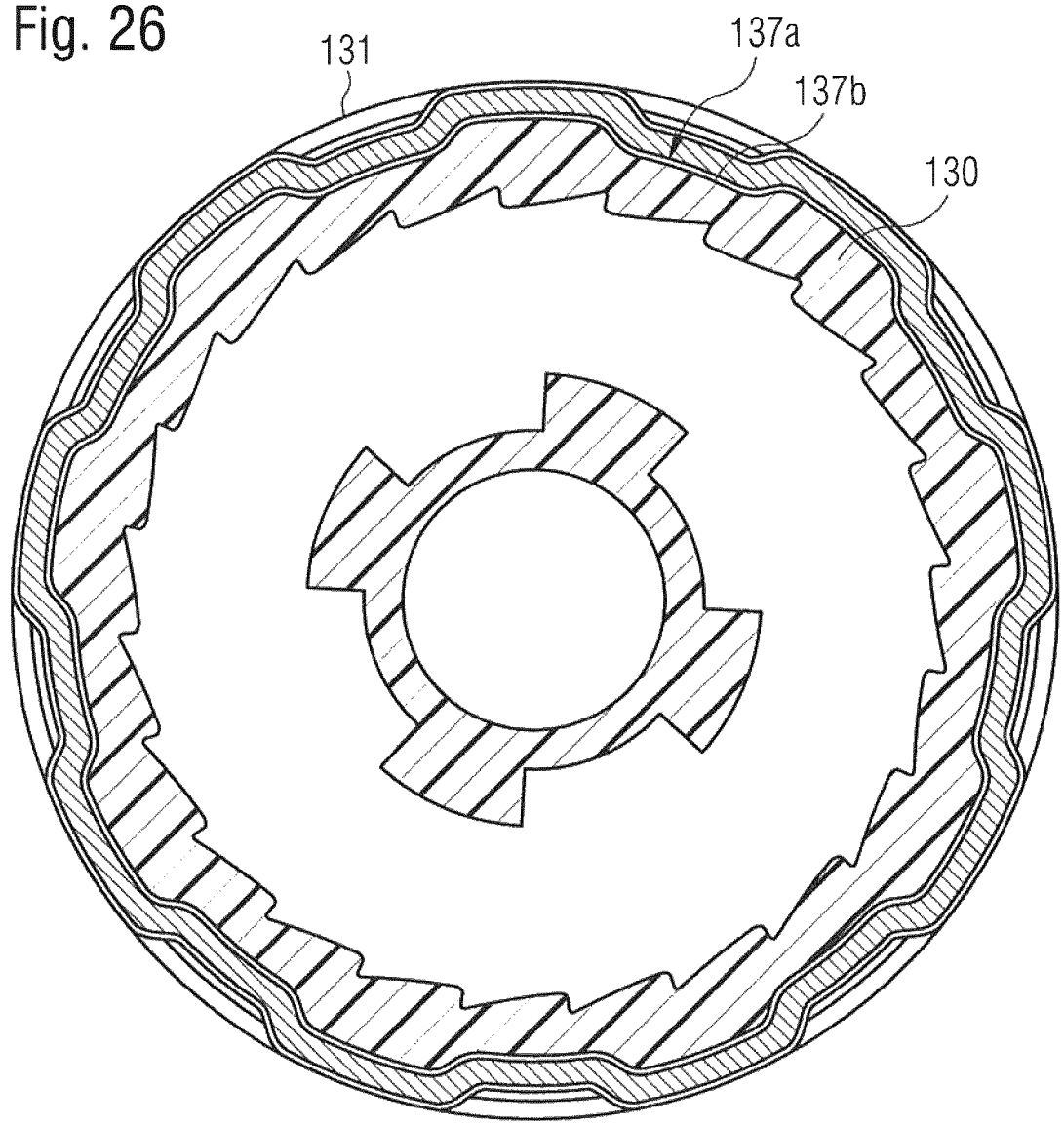
FIG. 26 schematically shows a cut-away view of the assembled dose button of FIG. 22b.

The plastic component 130 further comprises a grip feature 137b (FIGS. 25b and 26). The metal component 131 comprises a mating grip feature 137a. The grip feature 137b of the plastic component 130 comprises a plurality of grooves which are arranged along the outer surface of the plastic component 130. In this embodiment, the grip feature 137b comprises nine grooves. However, there may be embodiments with more than nine grooves, e.g. ten or twelve grooves, or less than nine grooves, e.g. five grooves. The grooves are, in particular, arranged along a side face of the proximal portion 130b (FIG. 22b). The grooves are adapted and arranged to receive the corresponding grip feature 137a of the metal component 131 (FIGS. 25a and 26).

The grip feature 137a of the metal component 131 comprises a plurality of grooves and ribs arranged along the side face of the metal component 131. In particular, the outer face of the metal component 131 may be compressed or formed, for example, thus creating grooves on the side surface and corresponding ribs on the inner side face of the metal component 131 as can be seen in FIG. 26 In other words, the outer and inner side faces of the metal component 131 may comprise a wave-like structure.

When the button 70 is assembled, the grip features 137a and 137b mechanically cooperate with one another to align the plastic component 130 and the metal component 131. In particular, when the button 70 is assembled, the ribs on the inner side face of the metal component 131 are guided in the grooves of the outer side face of the plastic component 130. Furthermore, the plastic component 130 and the metal component 131 are rotationally coupled due to mechanical cooperation of the grip features 137a, 137b. The grip feature 137a further enables the user to easily grip the outer surface of the button 70 for rotating the button 70 during operation of the device 1.

The metal component 131 and the plastic component 130 are preferably non-releasably coupled to one another. The metal component 131 and the plastic component are clamped to one another. The previously mentioned aperture 131a or open end has a diameter. The open end has a circumferentially extending tip 140 (FIGS. 22a, 22b and 24) delimiting the aperture 131a. Before assembling the button 70, the diameter of the aperture 131a is large enough to receive the plastic component 130, in particular the proximal portion 130b of the plastic component 130 (see FIG. 22a). In other words, before assembling the button 70, the diameter of the aperture 131a is greater than a maximum diameter of the proximal portion 130b of the plastic component 130. After the button 70 is finally assembled, i.e. after the plastic component 130 and the metal component 131 are non-releasably connected to one another, the diameter of the aperture 131a is smaller than the maximum outer diameter of the proximal portion 130b of the plastic component 130.

In the following, the method of assembling the button 70 is described in detail in connection with FIGS. 22a, 22b, 23 and 24:

At first, the plastic component 130 is provided. Furthermore, a metal sheet is provided. In a next step, the metal sheet is deep drawn. After the deep drawing, the metal sheet comprises an end face which is perpendicular with respect to a longitudinal axis of the metal sheet. This end face delimits the previously described aperture 131a.

The metal sheet is then formed in a tubular shape for providing the aperture 131a or open end at the distal end. At this assembly step, the aperture 131a is large enough to receive the plastic component 130 during the assembly process. In further steps, the grip feature 137a and the cut-outs 138 are provided by stamping and/or punching. Afterwards, the deep drawn metal sheet is anodised.

Now, the plastic component 130, in particular the proximal portion 130b, is inserted into the aperture 131a of the metal component 131. The plastic component 130 is inserted such that, when the plastic component 130 has reached its final position with respect to the metal component 131, the cut-outs 138 and the protrusions 139 can engage for aligning the metal component 131 and the plastic component 130.

Moreover, when the plastic component 130 is inserted, the grip features 137a, 137b engage one another for aligning the plastic component 130 and the metal component 131. Furthermore, the grip features 137a, 137b help to rotationally couple the metal component 131 and the plastic component 130 when the device is in use.

The plastic component 130 is moved with respect to the metal component 131 in the proximal direction, the grip features 137a, 137b guiding the movement. When the plastic component 130 has reached its final position with respect to the metal component 131, the proximal end face of the plastic component 130 mechanically cooperates with an inner surface of the proximal end face of the metal component 131, thereby hiding a gate point 136 (FIG. 25b) arranged at the proximal end face of the plastic component 130. When the plastic component 130 has reached its final position with respect to the metal component 131, the cut-outs 138 mechanically cooperate with the protrusions 139, thus ensuring absolute rotational alignment of the plastic component 130 and the metal component 131. These protrusions 139 and cut-outs 138 also act to transfer torque between the two components 130, 131 when the device is in use.

Figure 23:
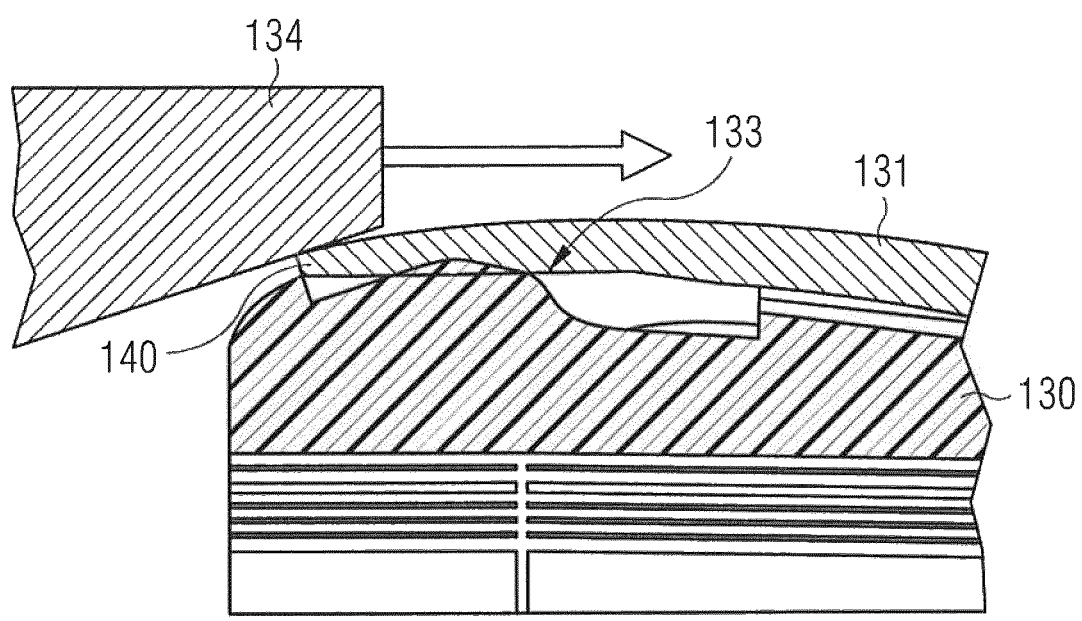
Figure 24:
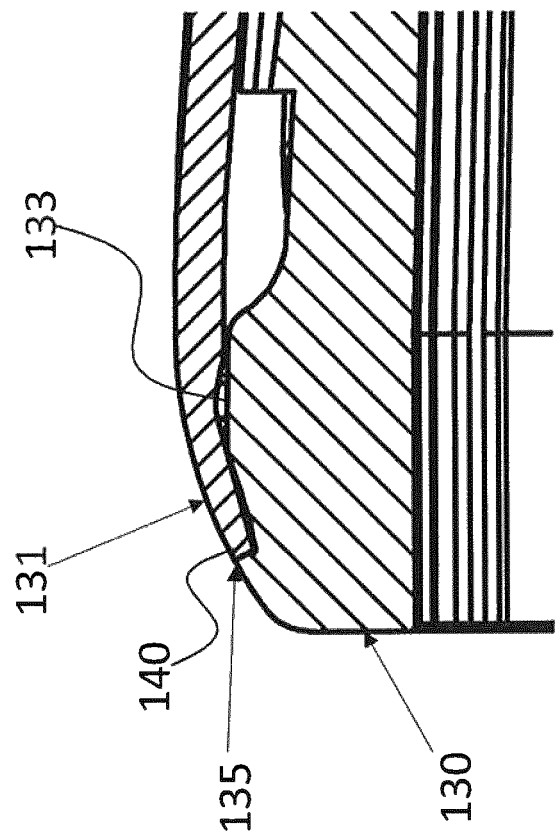
FIG. 24 schematically shows a part of the dose button of FIG. 22b in an assembled state.

When the plastic component 130 has reached the final position, the plastic component 130 and the metal component 131 are secured, preferably non-releasably secured, to one another. In particular, the plastic component 130 and the metal component 131 are clamped to each other. For this purpose, a swaging tool 134 is provided (FIG. 23). The swaging tool 134 may be conical. By means of the swaging tool 134, the open distal end is compressed such that the tip 140 is formed in (FIG. 22b).

The swaging tool 134 exerts a force onto the distal end of the metal component 131. The force is directed partially at least in the radial inward direction. Thereby, the plastic component 130, is elastically deformed in the radial inward direction either through contact with the metal component 131 or through direct contact with the swaging tool. The plastic component 130 comprises a bump feature 133. The bump feature 133 is arranged circumferentially around the outer surface of the plastic component 130, in particular the proximal portion 130b. During final assembly of the button 70, the distal end of the metal component 131 is swaged over the bump feature 133 around the full circumference, thus clamping it into place. Thereby, the tip 140 is plastically deformed in the radial inward direction to create a smooth surface of the button 70.

The plastic component 130 comprises an engaging feature 135. The engaging feature 135 may be a lip. The engaging feature 135 is arranged on the outer surface of the plastic component, in particular of its proximal portion 130b. The engaging feature 135 extends circumferentially around the proximal portion 130b. When the proximal portion 130b is completely inserted into the metal component 131, the engaging feature 135 is arranged in a position to mechanically cooperate with the distal end of the metal component 131 (FIG. 22a). When the distal end of the metal component 131 is plastically deformed during final assembly, the tip 140 is formed in and, thus, mechanically cooperates with the engaging feature 135, as can be seen in FIG. 22b and in FIG. 24. The engaging feature 135 prevents access to the tip 140 such that the user cannot gain a purchase under the edge of the metal component 131 to attempt to remove it from the plastic component 130.

When force is no longer exerted onto the metal component 131, the plastic component 130 at least partly flexes back in the radial outward direction, thereby ensuring a tight interface between the plastic component 130 and the metal component 131. The smooth anodized finish and negative taper of the metal component 131 make it extremely difficult if not impossible to gain the necessary traction to remove the metal component 131 from the plastic component 130 by hand and without using tools. Now, the button 70 is ready for being assembled to the further components of the device 1.

The assembled button 70 is retained by the clutch 90 to transfer the actions of the user to the clutch 90. For this purpose, the plastic component 130, in particular the central portion 130a, comprises four arms 73 which protrude in the distal direction. The arms 73 comprise hook-like snap features 74 at their respective distal ends. The arms 73 form splined surfaces engaging with the clutch 90 to transfer torque from the button 70 through the clutch 90 to the dial sleeve 62 and the proximal drive sleeve 42.

For mechanically coupling the clutch 90 and the button 70, the arms 73 are inserted into the clutch 90. When the arms 73 are inserted, the snap features 74 engage apertures or snap features 93 in the clutch 90. The snap features 74 are designed with angled undercut faces to maintain engagement when an axial load is applied to pull the button 70 out of the pen body 10. The space between the arms 73 defines pockets giving clearance for the flexible arms 48 of proximal drive sleeve 42 to slide freely relative to the button 70 and the clutch 90 when the button 70, in particular the metal component 131, is depressed and released during dose dispense.

The plastic component 130 further comprises the previously mentioned ratchet feature 132. The ratchet feature 132 is arranged on an inner surface of the plastic component 130 (see FIGS. 16 and 21b). The ratchet feature 132 comprises a plurality of ratchet teeth 71. The ratchet teeth 71 engage the ratchet arm 68 on the dial sleeve 62 (FIGS. 7a and 7b), which serves as the dispensing clicker giving audible feedback (ratchet clicks). The plastic component 130 further comprises an end face 72 (FIG. 16) which serves as the dose completion stop face with the outer body 10. This end face 72 thus serves to define the end position during dispense when it contacts the outer body 10 to provide a positive stop improving dose accuracy.

The cartridge holder 80 attaches to the inner body 20 with a bayonet connection 82 and houses the glass ampoule or cartridge 81 containing the medication to be dispensed. The cartridge holder 80 includes an aperture 83 in the rear face (as seen in FIG. 6) which if gripped by the user prevents the ampoule from falling out when the cartridge holder is removed from the inner body 20. The front face is printed with a dose number scale. The threaded distal end 84 is used to attach disposable pen needles.

The tubular clutch 90 is provided between the display member 60 and the button 70. The clutch 90 is fixed relative to and retains the button 70 as described above and together they travel axially relative to the proximal drive sleeve 42 when the button 70 is depressed during dispense, disengaging the clutch teeth from the dial sleeve 62. It also transfers torque from the button 70 to the proximal drive sleeve 42, and the dialing and 0 U/80 U stop loads from the button via the clutch teeth to the dial sleeve and number sleeve.

Drive sleeve splines 91 provided on an inner surface of the clutch 90 engage with the proximal drive sleeve 42. At the distal end face, clutch biasing teeth 92 are provided which mate with similar teeth on the proximal clicker part 102 to ensure that in the button out position (dialed dose) the clutch is locked in rotation to the proximal clicker part 102 under the biasing action of the clutch spring 103. The teeth 92 are shallow in height to prevent the proximal clicker part 102 from engaging with splines on the proximal drive sleeve 42 during dialing. Four snap apertures or snap features 93 serve to retain the snap features 74 of the plastic component 130 of the button 70, as described above. Near its proximal end, the clutch has splines 94 which at the end of dispense with the button 70 depressed lock to the inner body 20 to prevent the user from rotating the button 70 below the 0 U position.

Clutch teeth 95 engage with clutch teeth 65 of the dial sleeve to rotationally couple the button 70 via the clutch 90 to the number sleeve 61. During dispense the clutch is moved axially so as to disengage these clutch teeth 95 releasing the dial sleeve 62 to rotate back into the device whilst the clutch 90 and hence driver 40 move axially to dispense the dose.

The clicker 100 comprises a distal clicker part 101, a proximal clicker part 102 and a spring 103. The clutch spring 103 serves to bias the button 70 out so that at the end of a dose the button 70 pops out, re-engaging the clutch 90 with the dial sleeve 62 ready for dialing. Further, it provides the spring force for the clicker components to act as clickers and also as detent positions for the number sleeve 61. In addition, it holds the two halves of the drive sleeves 41, 42 in rotational engagement during dialing and dispense, whilst allowing them to disengage during device reset.

The distal clicker part 101 is permanently splined to the proximal drive sleeve 42 and engages with the proximal clicker part 102 which in turn is splined to the inner body 20. During dialing when the drive sleeve is rotated relative to the inner body, the two clickers 101, 102, rotate relative to each other under the compression force of the clutch spring 103. This force combined with the clicker teeth formed on the end face of each clicker provides the clicks and also the detent dialing positions.

During dispense the two clickers 101, 102 are pressed together under the dispense load and therefore prevent relative rotation between the proximal drive sleeve 42 and inner body 20, driving the piston rod forwards to deliver the dose. The splines 104 on the inner bore rotationally couple the distal clicker part 101 to the proximal drive sleeve 42 at all times, but allow free axial movement when the button 70 is depressed during dispense and when the two clickers ride over each other during dialing. The profile of the clicker teeth 105, 106 on both distal clicker part 101 and proximal clicker part 102 are identical and ride over each other under the compressive load from the spring 103 during dialing.

The proximal clicker part 102 is permanently splined to the inner body 20 by external splines 107 which prevent relative rotation with the inner body during both dialing and dispense, providing clicks during dialing and locking the proximal drive sleeve 42 in rotation during dispense. Additional cylindrically shaped splines 108 also couple the proximal clicker part 102 rotationally to the proximal drive sleeve 42 when the button 70 is depressed, this preventing the user from dialing past 80 units with the button depressed. Proximal clicker part 102, in addition to the primary clicker teeth 106, has clutch biasing teeth 109 on the opposite end face. These teeth mate with similar teeth 92 on the clutch to ensure that in the button out position (dialed dose) the clutch is locked in rotation to the proximal clicker part 102 under the biasing action of clutch spring 103.

The cartridge bias spring 110 is assembled as two components one after the other, the lower first and the upper second. The spring combination serves to apply an end load to the cartridge 81 at extremes of tolerance so as to bias it forwards onto the end face of the ferrule in the cartridge holder 80. This ensures that when the user removes and attaches a needle, the friction between the needle cannula and septum of the cartridge does not move the cartridge 81 axially relative to the cartridge holder 80. The bias spring 110 also acts to provide a force against which the user has to connect the cartridge holder 80 and this may add to the tactile feedback of this bayonet joint. The spring 100 also serves to eject the cartridge holder 80 if the cartridge holder is not rotated into a secure position, highlighting this error to the user.

The cap 120 serves to protect the cartridge holder 80 from damage and the cartridge 81 itself from dust dirt ingress on to the area around the septum. The cap is designed to accommodate a standard pen injector needle.

The window insert 230 may include a lens to magnify the dose numbers e.g. by approximately 25% from their printed size. The window insert 230 may be back printed to protect the printed surface from abrasion and also to maximize the light entering through the window aperture, giving uniform illumination of the dose numbers and white area around these numbers. Arrows may be printed adjacent to the window aperture that indicate the dose dialed.

In the following, the function of the drug delivery device and its components will be explained in more detail with reference to FIGS. 17 to 19.

To use the device, a user has to select a dose. In the start (at rest) condition as shown in FIG. 17 the display member 60 indicates the number of doses dialed to the user. The number of dialed units can be viewed through the dose window 230 in the outer body 10. Due to the threaded engagement between the display member 60 and the inner body 20, rotation of the button 70 in a clockwise fashion causes the display member 60 to wind out of the device and incrementally count the number of units to be delivered. FIG. 18 shows an intermediate stage of dialing (e.g. 7 of 80 units).

During dose setting the button 70, the driver 40 and the display member 60 are rotationally locked together via the clutch 90. Further, the button 70, the driver 40 and the display member 60 are axially coupled. Thus, these three components wind out of the outer housing 10 during dose setting. Clockwise rotation of the button 70 causes the driver 40 to rotate and in doing so it advances along the piston rod 30 which remains fixed throughout dialing. The clicker arrangement 100 provides tactile and audible feedback to the user when dialing doses. At the maximum settable dose of 80 units, the stop features 12 and 67 engage to prevent further dialing.

The last dose nut 50 provides the function of counting the number of dispensed units. The nut 50 locks the device 1 at the end of cartridge life and as such no more drug can be dialed by the user. The last dose nut 50 and the driver 40 are connected via a threaded interface as explained above. Further, the last dose nut 50 is assembled into splines 22 such that the nut 50 and the inner body 20 are rotationally locked together (at all times). Rotation of the driver 40 during dialing causes the nut 50 to advance along the thread 44. The nut 50 is free to slide axially within the inner body 20 at all times which allows advancement of the nut. The change in pitch of thread 44 shown in FIG. 9 towards the final doses axially accelerates the advancement of the nut 50 towards the end of cartridge life lockout condition. At the end of life condition, the stop features 51 of the last dose nut 50 contact the corresponding features 45 on the driver 40. The splined contact with inner body 20 reacts any torque transmitted by these stop features 45.

With the desired dose dialed, the device 1 is ready for dose dispensing. This basically requires pushing the button 70 and, in particular the metal component 131, which will result in a disengagement of the clutch 90 from dial sleeve 62 thus allowing relative rotation between the display member 60 and the button 70. In all conditions the driver 40 and the button 70 are rotationally locked together by engagement of arms 73 and fingers 48 and by splines 91 engaging corresponding splines on proximal drive sleeve 42. Thus, with the clutch 90 disengaged (button 70 pushed in), the button 70 and the driver 40 are rotationally locked together with the button 70, the driver 40 and the display member 60 still being axially coupled.

When dispensing a dose, the dose button 70 and clutch 90 are moved axially relative to the mechanism compressing the clutch spring 103. Because the proximal clicker part 102 is splined to the inner body 20 and the axial load passing through the clicker teeth 105, 106 locks the distal clicker part 101 in rotation to the proximal clicker part 102, the mechanism is forced to move axially whilst the dial sleeve 62 and number sleeve 61 are free to spin back into the outer housing 10. The interaction of mating threads between the piston rod 30, driver 40 and inner body 20 delivers a mechanical advantage of 2:1. In other words, axially advancing driver 40 causes the piston rod 30 to rotate which due to the threaded engagement of piston rod 30 with the inner body 20 advances the piston rod. During dose dispensing dispense clicker 68, 71 is active which involves button 70 and display member 60. The dispense clicker provides primarily audible feedback to the user that drug is being dispensed.

The end of this step is shown in FIG. 19. At this point the dose is complete and when the user removes the force from the end of the dose button 70, the clutch spring 103 pushes this dose button 70 rearwards, re-engaging the teeth 65 and 95 between the clutch and the dial sleeve.

Resetting the device starts with removal of the cartridge holder 80 and replacing an empty cartridge with a full cartridge 81. As the cartridge holder is re-attached, the bung of the new cartridge contacts bearings 31, thus pushing piston rod 30 back into the housing. Initially, the piston rod 30 screws into the inner body 20, thereby axially disengaging the coupler 43 from the proximal drive sleeve 42 against the biasing force of spring 103. Once disengaged the coupler 43 is free to start rotating together with distal drive sleeve 41 and continues to do so as the cartridge holder 80 is moved axially into engagement with the inner body 20. Thus, the distal drive sleeve 41 rotates with respect to the proximal drive sleeve 42 which is still rotationally constrained in inner body 20 as clicker parts 101 and 102 are pressed together by compressed spring 103. As the distal drive sleeve 41 rotates, last dose nut 50 is reset to its (distal) start position. Coupling the cartridge holder 80 to inner body 20 backs off the mechanism due to the bayonet structure 23 allowing re-engagement of the proximal drive sleeve 42 with coupler 43 and thus the distal drive sleeve 41.

The scope of protection is not limited to the examples given herein above. The invention is embodied in each novel characteristic and each combination of characteristics, which particularly includes every combination of any features which are stated in the claims, even if this feature or this combination of features is not explicitly stated in the claims or in the examples. The features of the embodiments mentioned above may be combined. The layout, function, and number of components may be changed in other embodiments.

REFERENCE NUMERALS 1 drug delivery device
10 outer housing part 11 distal part
12 stop
13 aperture
20 inner body
21 external thread
22 splines
23 bayonet features
24 retaining means
25 stop
30 piston rod
31 bearing
32 thread
33 thread
40 driver
41 distal portion
42 proximal portion
43 coupler
44 thread
45 stop faces
46 splines
47 teeth features
48 fingers
49 bearing surface
50 dose nut
51 stop faces
52 external ribs
53 internal thread
60 display member
61 number sleeve
62 dial sleeve
63 stop face
64 thread
65 teeth
66 contact features
67 opposite faces
68 clicker
70 button
71 ratchet teeth/clicker
72 end face
73 arms
74 snap features
80 cartridge holder
81 cartridge
82 bayonet connection
83 aperture
84 distal end
90 clutch
91 drive sleeve splines
92 clutch biasing teeth
93 snap features
94 splines
95 clutch teeth
100 clicker
101 distal clicker part
102 proximal clicker part
103 spring
104 splines
105, 106 clicker teeth
107 external splines
108 shaped splines
109 clutch biasing teeth
110 spring
120 cap
121 distal end
122 proximal end
230 window
130 plastic component
130a central portion
130b outer or proximal portion
131 metal component
131a aperture
132 ratchet feature
133 bump feature
134 swaging tool
135 engaging feature
136 gate point
137a grip feature
137b grip feature
138 cut-out
139 protrusion
140 tip

The invention claimed is:

1. A drug delivery device comprising:
a reservoir with a drug or a reservoir retainer configured to retain a reservoir with a drug,
a button for setting and dispensing a dose of the drug from the drug delivery device, the button comprising:
a plastic component; and
a metal component,
wherein the plastic component is at least partly received by the metal component, and wherein the metal component is configured to be manipulated by a user for setting and dispensing the dose,
wherein the button is configured to move relative to the reservoir or the reservoir retainer during setting of the dose and during dispensing of the dose,
wherein the metal component and the plastic component are rotationally coupled to one another, wherein the plastic component comprises at least one protrusion and the metal component comprises at least one cut-out, wherein the at least one protrusion is received by the at least one cut-out for rotationally coupling and/or aligning the plastic component and the metal component.

2. The drug delivery device according to claim 1, wherein the at least one cut-out is a plurality of cut-outs and the at least one protrusion is a plurality of protrusions, each protrusion of the plurality of protrusions being received in an associated cut-out of the plurality of cut-outs.

3. The drug delivery device according to claim 1, wherein the cut-out is provided in a proximal end surface of the metal component and the protrusion, which is received by the cut-out, protrudes proximally from the proximal end surface of the metal component.

4. The drug delivery device according to claim 1, wherein the metal component comprises an aperture with a diameter large enough to receive the plastic component at least in part, and wherein the aperture is provided at a distal end of the metal component.

5. The drug delivery device according to claim 4, wherein the diameter of the aperture is smaller than the maximum outer diameter of the plastic component.

6. The drug delivery device according to claim 5, wherein the plastic component is elastically deformed in a radial direction.

7. The drug delivery device according to claim 1, wherein the plastic component comprises a bump feature, which is arranged on an outer surface of the plastic component and extends circumferentially along the outer surface of the plastic component, and wherein the metal component is swaged over the bump feature.

8. The drug delivery device according to claim 1, wherein the metal component defines a portion of a proximal end surface of the button, the portion being pressable for dispensing the dose by the user.

9. The drug delivery device according to claim 1, wherein the metal component comprises an aperture for receiving the plastic component, and wherein a diameter of the aperture is smaller than a maximum outer diameter of the plastic component.

10. The drug delivery device according to claim 1, wherein the plastic component is at least in part elastically deformable.

11. The drug delivery device according to claim 1, wherein the metal component is formed over the plastic component.

12. The drug delivery device according to claim 1, wherein the metal component is swaged to clamp the plastic component.

13. The drug delivery device according to claim 1, wherein the plastic component comprises at least one grip feature and the metal component comprises at least one mating grip feature, wherein the grip features are adapted and arranged for aligning the plastic component and the metal component when the plastic component is received by the metal component.

14. The drug delivery device according to claim 1, wherein the metal component is deep drawn.

15. The drug delivery device according to claim 1, wherein the drug delivery device is a reusable drug delivery device.

16. The drug delivery device according to claim 1, wherein the drug delivery device comprises a rotatable sleeve, and wherein the plastic component comprises at least one ratchet feature arranged on an inner surface of the plastic component, wherein the at least one ratchet feature is adapted and arranged to mechanically cooperate with the rotatable sleeve during dose delivery to provide an audible feedback.

17. The drug delivery device according to claim 1, comprising a drive mechanism, wherein the plastic component comprises at least one snap feature adapted and arranged to mechanically cooperate with the drive mechanism of the drug delivery device for rotationally coupling the button and the drive mechanism.

18. The drug delivery device according to claim 1, comprising a drive mechanism, wherein the plastic component comprises at least one snap feature adapted and arranged to mechanically cooperate with the drive mechanism of the drug delivery device for axially coupling the button and the drive mechanism.

19. The drug delivery device according to claim 1, comprising a drive mechanism, wherein the plastic component comprises at least one snap feature adapted and arranged to mechanically cooperate with the drive mechanism of the drug delivery device for rotationally and axially coupling the button and the drive mechanism.

* * * * *